United States Patent
Iyer et al.

(10) Patent No.: US 8,575,198 B1
(45) Date of Patent: Nov. 5, 2013

(54) IN-PROCESS CONTROL FOR THE MANUFACTURE OF GLATIRAMER ACETATE

(75) Inventors: Mani S. Iyer, North Chelmsford, MA (US); Harper Kaminski, Somerville, MA (US)

(73) Assignee: Momenta Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 13/607,625

(22) Filed: Sep. 7, 2012

Related U.S. Application Data (60) Provisional application No. 61/532,079, filed on Sep. 7, 2011.

(51) Int. Cl.
*A61K 38/00* (2006.01)
*C07K 1/04* (2006.01)

(52) U.S. Cl.
USPC ........... 514/333; 514/335; 514/336; 514/337; 514/885

(58) Field of Classification Search
None
See application file for complete search history.

(56) References Cited

U.S. PATENT DOCUMENTS

| | | | |
|---|---|---|---|
| 3,849,550 A | 11/1974 | Teitelbaum et al. |
| 5,112,810 A | 5/1992 | Nagai et al. |
| 5,800,808 A | 9/1998 | Konfino et al. |
| 5,981,589 A | 11/1999 | Konfino et al. |
| 6,048,898 A | 4/2000 | Konfino et al. |
| 6,054,430 A | 4/2000 | Konfino et al. |
| 6,342,476 B1 | 1/2002 | Konfino et al. |
| 6,362,161 B1 | 3/2002 | Konfino et al. |
| 6,514,938 B1 | 2/2003 | Gad et al. |
| 6,620,847 B2 | 9/2003 | Konfino et al. |
| 6,800,287 B2 | 10/2004 | Gad et al. |
| 6,821,745 B2 | 11/2004 | Smith |
| 6,844,314 B2 | 1/2005 | Eisenbach-Schwartz et al. |
| 6,939,539 B2 | 9/2005 | Konfino et al. |

(Continued)

FOREIGN PATENT DOCUMENTS

| | | |
|---|---|---|
| EP | 1 408 066 | 4/2004 |
| EP | 2 143 728 | 1/2007 |

(Continued)

OTHER PUBLICATIONS

Hans Ulrich Moritz. Increase in Viscosity and its Influence on Polymerization Processes. Chem. Eng. Technol. 12 (1989) 71-87.*

(Continued)

*Primary Examiner* — Karlheinz R Skowronek
*Assistant Examiner* — Jia-Hai Lee
(74) *Attorney, Agent, or Firm* — Fish & Richardson P.C.

(57) ABSTRACT

The present disclosure provides methods for manufacturing or producing glatiramer acetate having a Mp of 5000-9000 Da. These methods include: polymerizing N-carboxy anhydrides of L-alanine, benzyl-protected L-glutamic acid, trifluoroacetic acid (TFA)-protected L-lysine, and L-tyrosine to generate a sample comprising intermediate-1; treating the sample comprising intermediate-1 to partially depolymerize the protected copolymer and deprotect benzyl-protected L-glutamic acid, measuring the viscosity of the sample comprising intermediate-1 during the treatment, and ending the treatment when the viscosity of the sample is within an endpoint range, thereby generating a sample comprising intermediate-2; treating the sample comprising intermediate-2 to deprotect TFA-protected L-lysine, thereby generating intermediate-3; further processing the intermediate-3 to generate a sample glatiramer acetate; and purifying the glatiramer acetate to generate a composition comprising purified glatiramer acetate having a Mp of 5000-9000 Da.

30 Claims, 2 Drawing Sheets

(56) References Cited

U.S. PATENT DOCUMENTS

| | | | |
|---|---|---|---|
| 7,022,663 | B2 | 4/2006 | Gilbert et al. |
| 7,033,582 | B2 | 4/2006 | Yong et al. |
| 7,041,472 | B2 | 5/2006 | Norioka et al. |
| 7,049,399 | B2 | 5/2006 | Bejan et al. |
| 7,053,043 | B1 | 5/2006 | Aharoni et al. |
| 7,074,580 | B2 | 7/2006 | Gad et al. |
| 7,163,802 | B2 | 1/2007 | Gad et al. |
| 7,199,098 | B2 | 4/2007 | Konfino et al. |
| 7,329,353 | B2 | 2/2008 | Dillon et al. |
| 7,427,600 | B2 | 9/2008 | Mickle et al. |
| 7,495,072 | B2 | 2/2009 | Dolitzky |
| 7,560,100 | B2 | 7/2009 | Pinchasi et al. |
| 7,615,359 | B2 | 11/2009 | Gad et al. |
| 7,732,162 | B2 | 6/2010 | Hoffman et al. |
| 7,884,187 | B2 | 2/2011 | Zhu et al. |
| 7,906,153 | B2 | 3/2011 | Theoharides |
| 7,968,511 | B2 | 6/2011 | Vollmer |
| 8,008,258 | B2 | 8/2011 | Aharoni et al. |
| 8,058,235 | B1 | 11/2011 | Coleman et al. |
| 2002/0115103 | A1 | 8/2002 | Gad et al. |
| 2003/0064914 | A1 | 4/2003 | Konfino et al. |
| 2003/0153007 | A1 | 8/2003 | Chen et al. |
| 2003/0170729 | A1 | 9/2003 | Klinger |
| 2004/0091956 | A1 | 5/2004 | Bejan et al. |
| 2004/0106554 | A1 | 6/2004 | Konfino et al. |
| 2005/0038233 | A1 | 2/2005 | Gad et al. |
| 2005/0171286 | A1 | 8/2005 | Konfino et al. |
| 2006/0052586 | A1 | 3/2006 | Dolitzky |
| 2006/0058225 | A1 | 3/2006 | David et al. |
| 2006/0154862 | A1 | 7/2006 | Ray et al. |
| 2007/0021324 | A1 | 1/2007 | Dolitzky |
| 2007/0054857 | A1 | 3/2007 | Pinchasi et al. |
| 2007/0059798 | A1 | 3/2007 | Gad et al. |
| 2007/0141663 | A1 | 6/2007 | Ding et al. |
| 2007/0161566 | A1 | 7/2007 | Pinchasi |
| 2007/0178113 | A1 | 8/2007 | Backstrom et al. |
| 2008/0118553 | A1 | 5/2008 | Frenkel et al. |
| 2008/0220441 | A1 | 9/2008 | Birnbaum et al. |
| 2008/0319092 | A1 | 12/2008 | Singh |
| 2009/0099130 | A1 | 4/2009 | Demetriou et al. |
| 2009/0263347 | A1 | 10/2009 | Jing et al. |
| 2010/0036092 | A1 | 2/2010 | Hsiao et al. |
| 2010/0040537 | A1 | 2/2010 | Gu et al. |
| 2010/0111952 | A1 | 5/2010 | Beckman et al. |
| 2010/0234566 | A1 | 9/2010 | Ray et al. |
| 2010/0256039 | A1 | 10/2010 | Coleman et al. |
| 2010/0324265 | A1 | 12/2010 | Kota et al. |

FOREIGN PATENT DOCUMENTS

| | | |
|---|---|---|
| EP | 2 046 817 | 12/2009 |
| WO | WO95/31990 | 11/1995 |
| WO | WO03/048735 | 6/2003 |
| WO | WO2004/043995 | 5/2004 |
| WO | WO2006/029393 | 3/2006 |
| WO | WO2006/029411 | 3/2006 |
| WO | WO2006/050122 | 5/2006 |
| WO | WO2006/069739 | 7/2006 |
| WO | WO2006/069765 | 7/2006 |
| WO | WO2006/083608 | 8/2006 |
| WO | WO2007/030573 | 3/2007 |
| WO | WO2007/127977 | 11/2007 |
| WO | WO2007/146331 | 12/2007 |
| WO | WO2008/006026 | 1/2008 |
| WO | WO 2009/129018 A1 * | 10/2009 |
| WO | WO2010/017292 | 2/2010 |
| WO | WO2010/072418 | 7/2010 |
| WO | WO2010/115175 | 10/2010 |
| WO | WO2012/016042 | 2/2012 |

OTHER PUBLICATIONS

Aventis Pharmaceuticals, Inc., National Drug Code (NDC) 0088-1153-30 (Copaxone®) Label, Version 1 (published Jul. 25, 2006).

Varkony, H., et al, "The glatiramoid class of immunomodulator drugs," Expert Opinion on Pharmacotherapy (Mar. 2009) 10(4):657-668.

Schechter, Bilha; Schechter, Israel; Ramachandran, J., Conway-Jacobs, A., "Synthetic antigens with sequential and conformation-dependent determinants containing the same L-tyrosyl-L-alanyl-L-glutamyl sequence," Eur J Biochem (1971) 20:309-320.

Teitelbaum, D., et al, "Suppression of experimental allergic encephalomyelitis by a synthetic polypeptide," Eur J Immunol (1971) 1(4):242-248.

Sorup, Per, Junager, Finn, and Hvidt, Aase, "Physicochemical studies of a branched polypeptide antigen: poly(1-Tyr,1-Glu)-poly(dl-Ala)—poly(1-Lys)," Biochimica et Biophysica Acta (BBA)—Protein Structure (Sep. 27, 1977) 494(1):9-18.

Hirschmann, Ralph, Schwam, Harvey, Strachan, R.G., "Controlled synthesis of peptides in aqueous medium. VIII. Preparation and use of novel .alpha.-amino acid N-carboxyanhydrides," J Am Chem Soc (1971) 93(11):2746-2754.

Sela, M., Fuchs, S., Arnon, R, "Studies on the chemical basis of the antigenicity of proteins, 5. Synthesis, characterization and immunogenicity of some multichain and linear polypeptides containing tyrosine," Biochem J (1962) 85:223-235.

Teitelbaum, D., Arnon, R., Sela, M., "Copaxone," Comprehensive Medicinal Chemistry II (2007) 8:173-185.

Deming, Timothy J., "Synthetic polypeptides for biomedical applications," Progress in Polymer Science (Aug.-Sep. 2007) 32(8-9):858-875.

Johnson, Kenneth, "Glatiramer acetate for treatment of relapsing-remitting multiple sclerosis," Expert Review of Neurotherapeutics (Apr. 2012) 12(4):371-384.

Suzuki et al., Quantitative Analysis of Pyroglutamic Acid in Peptides, J. Agric. Food Chem., 47(8):3248-3251 (1999).

Bogunovic et al., "Comparative Quantitative Mass Spectrometry Analysis of MHC Class II-Associated Peptides Reveals a Role of GILT in Formation of Self-Peptide Repertoire," PLoS One 5(5):e10599 (2010) http://www.plosone.org/article/info%3Adoi%2F10.1371%2Fjournal.pone.0010599.

Busby et al., "An Enzyme(s) That Converts Glutaminyl-peptides into Pyroglutamyl-peptides," The Journal of Biological Chemistry, The American Society of Biological Chemists, Inc., 262(18):8532-8536 (1987).

Gawlik et al., "Autocatalytic Activation of the Furin Zymogen Requires Removal of the Emerging Enzyme's N-Terminus from the Active Site," PLoS ONE 4(4):e5031 (2009) http://www.plosone.org/article/info%3Adoi%2F10.1371%2Fjournal.pone.0005031.

Munton et al., "Qualitative and Quantitative Analyses of Protein Phosphorylation in Naïve and Stimulated Mouse Synaptosomal Preparations," American Society for Biochemistry and Molecular Biology, Brain Research Institute, Molecular & Cellular Proteomics, 6.2 (2006) Zurich Switzerland (http://www.mcponline.org/content/6/2/283.full).

Ozols, "Isolation and the complete amino acid sequence of luminal endoplasmic reticulum glucose-6-phosphate dehydrogenase," Procedures of the National Academy of Science, USA, 90:5302-5306 (1993).

Grimmelikhuujzen et al., "Isolation of <Glu-Gly-Arg-Phe-NH2 (AnthoRFamide), a neuropeptide from sea anemones (coelenterate/neurotransmitter/evolution/radioimmunoassay/HPLC)," Procedures of the National Academy of Science, USA, 83:9817-9821 (1986).

Qu et al., "Rapid determination of underivatized pyroglutamic acid, glutamic acid, glutamine and other relevant amino acids in fermentation media by LC-MS-MS," The Royal Society of Chemistry, Analyst (2002) http://www.rsc.org/delivery/_ArticleLinking/DisplayArticleForFree.cfm?doi=b108422b&JournalCode=AN.

Abdelaziz et al., "Inhibition of TNF-alpha production in THP-1 macrophages by glatiramer acetate does not alter their susceptibility to infection by Listeria monocytogenes and does not impair the efficacy of ampicillin or moxifloxacin against intracellular bacteria," J. Anitmicrobial Chem. 54(1):288-289, 2004.

Farina et al., "Treatment of multiple sclerosis with Copaxone (COP): Elispot assay detects COP-induced interleukin-4 and interferon-gamma response in blood cells," Brain 124(4):705-719, 2001.

Hartmann J. et al., "Formation of specific amino acid sequences during carbodiimide-mediated condensation of amino acids in aque- (56) References Cited

OTHER PUBLICATIONS ous solution, and computer-simulated sequence generation," Origins of Life, 14, ( 1-4): 213-220, 1984.

Li Q Q et al., "Glatiramer acetate inhibition of tumor necrosis factor-alpha-induced RANTES expression and release from U-251 MG human astrocytic cells," J. of Neurochem. 77(5):1208-1217, 2001.

Milo et al., "Additive effects of copolymer-1 and interferon beta-1b on the immune response to myelin basic protein," J. of Neuroimmunology 61(2):185-193, 1995.

Yang et al., "Drug Acyl Glucuronides: Reactivity and Analytical Implication," Curr. Pharmac. Analysis (Netherlands) 2(3):259-277, 2006.

Express Search, Inc., Accelerated Examination Search Letter, Apr. 18, 2012.

Blanchette, F., Neuhaus, O., "Glatiramer acetate: evidence for a dual mechanism of action," J Neurol (2008) 255(Supp 1):26-36.

Schrempf, W., Ziemssen, T., "Glatiramer acetate: mechanisms of action in multiple sclerosis," Autoimmun Rev (Aug. 2007) 6(7):469-475.

* cited by examiner

IN-PROCESS CONTROL FOR THE MANUFACTURE OF GLATIRAMER ACETATE

CROSS REFERENCE TO RELATED APPLICATIONS

This application claims the benefit under 35 U.S.C. §119(e) of the filing date of U.S. Provisional Application Ser. No. 61/532,079, filed Sep. 7, 2011, and which is incorporated here by reference.

TECHNICAL FIELD

The present disclosure relates to methods for making (e.g., manufacturing or producing) glatiramer acetate, including in-process or real-time assessment of reaction solution viscosity during the manufacture or production of glatiramer acetate.

BACKGROUND

Glatiramer acetate, marketed commercially as COPAXONE®, consists of the acetate salts of synthetic polypeptides containing four naturally occurring amino acids: L-glutamic acid, L-alanine, L-tyrosine, and L-lysine with a reported average molar fraction of 0.141, 0.427, 0.095, and 0.338, respectively and an average molecular weight of 5,000-9,000 Daltons. Chemically, glatiramer acetate is designated L-glutamic acid polymer with L-alanine, L-lysine and L-tyrosine, acetate (salt). Its structural formula is:

(Glu, Ala, Lys, Tyr)$_x$·xCH$_3$COOH
(C$_5$H$_9$NO$_4$·C$_3$H$_7$NO$_2$·C$_6$H$_{14}$N$_2$O$_2$·C$_9$H$_{11}$NO$_3$)$_x$·xC$_2$H$_4$O$_2$ CAS- 147245-92-9

SUMMARY

The present disclosure provides methods for determining reaction progression, during the manufacture or production of glatiramer acetate, using real-time or in-process assessment (e.g., monitoring, measurement, analysis, detection, determination, evaluation, and/or estimation) of reaction solution viscosity.

Described herein is a method for manufacturing glatiramer acetate drug substance having a Mp of 5000-9000 Da, the method comprising: (a) polymerizing N-carboxy anhydrides of L-alanine, benzyl-protected L-glutamic acid, trifluoroacetic acid protected L-lysine and L-tyrosine to generate a composition comprising intermediate-1; (b) treating the composition comprising intermediate-1 to partially depolymerize intermediate-1 and to deprotect benzyl-protected L-glutamic acid; (c) measuring the viscosity (e.g., the dynamic or absolute viscosity) of the composition during step (b); (d) ending step (b) when the viscosity of the composition is at a predetermined level (e.g., within a range shown in Table 1 when measured within a corresponding temperate range shown in Table 1) that informs that step (f) will yield glatiramer acetate with a Mp of 5000-9000 Da, thereby generating a composition comprising intermediate-2; (e) treating the composition comprising intermediate-2 to deprotect trifluoroacetic acid protected L-lysine, thereby generating a composition comprising intermediate-3; and (f) processing the composition comprising intermediate-3 to generate glatiramer acetate drug substance having a Mp of 5000-9000 Da.

In various embodiments: the viscosity is measured in-process during step (b); the viscosity is measured intermittently during at least a portion of step (b); the viscosity is measured continuously during at least a portion of step (b); is measured continuously during a substantial portion of step (b); and the viscosity is measured continuously during step (b); and the viscosity is measured in a sample off line.

In various embodiments: the predetermined level of viscosity is 77 cP to about 566 cP when viscosity is measured at 15° C. to 35° C.; the predetermined level of viscosity is 93 cP to about 498 cP at 15° C. to 35° C.; the predetermined level of viscosity is 103 cP to about 453 cP at 15° C. to 35° C.; the predetermined level of viscosity is 77 cP to about 566 cP when viscosity is measured at 15° C. to 35° C. and the density of the composition is 0.8-1.6 gm/ml; the predetermined level of viscosity is 77 cP to about 566 cP when viscosity is measured at 15° C. to 35° C. and the density of the composition is 1.0-1.4 gm/ml the temperate of the composition during step (b) is 15° C.-35° C.; the temperature of the composition during step (b) is 19° C.-25° C.; the concentration of Intermediate-1 at the start of step (b) is 7-11% on a weight/weight basis; and the density of the composition during step (b) is 0.8-1.6 gm/ml.

Some embodiments comprise ending step (b) when the viscosity (e.g., 200-300 cP at 20° C.-24° C.) of the composition is at a predetermined level that informs that step (f) will yield glatiramer acetate with a Mp of 7000-8000 Da (e.g., 7200-7400 Da).

In some cases the method further comprises: measuring the temperature of the composition during at least a portion of step (b); measuring both viscosity and temperature during at least a portion of step (b).

In some cases step (b) comprises holding a composition comprising Intermediate-1, phenol, HBr and acetic acid for a period of time; in some cases the composition further comprises water.

In some cases step (d) comprises quenching the reaction with water.

In some case step (b) comprises holding a composition comprising Intermediate-1, HBr and acetic acid in which Intermediate-1 is present at the start of step (b) at 7-11% on a weight/weight basis relative to entire the composition. In some cases the composition comprising Intermediate-1, HBr and acetic acid does not comprise water or contains only residual water from the production of Intermediate-1. In some cases the composition comprising Intermediate-1, HBr and acetic acid further comprises water (e.g., at 0.1-10% on a weight/weight basis relative to the entire composition or at 10-12% on a weight/weight basis relative to Intermediate-1 at the start of step (b)). Is some cases: step (b) is carried out at 19° C.-25° C., water is present during step (b) at 0.1%-10% on a weight/weight basis and Intermediate-1 is present at 7%-11% on a weight/weight basis at the start of step (b); and in some cases water is present during step (b) in a range selected from the group consisting of 5-25%, 13-19%, and 14-18% w/w against Intermediate-1 present at the start of step (b).

In some cases step (f) comprises filtering the composition comprising intermediate-3.

Also described is a method for preparing glatiramer acetate drug product comprising: (a) obtaining glatiramer acetate drug substance prepared by a method described herein; and (b) processing the glatiramer acetate drug substance to produce glatiramer acetate drug product. In some cases, the step of processing the glatiramer acetate drug substance to produce glatiramer acetate drug product comprises the addition of mannitol. In some cases the method further comprises: packaging the glatiramer acetate drug product. In some cases the method comprises ending step (b) when the viscosity of the sample is within a range shown in Table 1 when measured within a corresponding temperate range shown in Table 1.

In some aspects, the disclosure provides methods for manufacturing or producing a composition comprising purified glatiramer acetate having a Mp of 5000-9000 Da. In some embodiments, such methods include: polymerizing N-carboxy anhydrides of L-alanine, benzyl-protected L-glutamic acid, trifluoroacetic acid (TFA)-protected L-lysine, and L-tyrosine to generate a sample comprising intermediate-1; treating the sample comprising intermediate-1 to partially depolymerize the protected copolymer and deprotect benzyl-protected L-glutamic acid, measuring the viscosity of the sample comprising intermediate-1 during the treatment, and ending the treatment when the viscosity of the sample is within an endpoint range, thereby generating a sample comprising intermediate-2; treating the sample comprising intermediate-2 to deprotect TFA-protected L-lysine, thereby generating intermediate-3; further processing the intermediate-3 to generate a sample glatiramer acetate; and purifying the glatiramer acetate to generate a composition comprising purified glatiramer acetate having a Mp of 5000-9000 Da. In some embodiments, methods include: polymerizing N-carboxy anhydrides of L-alanine, benzyl-protected L-glutamic acid, trifluoroacetic acid (TFA)-protected L-lysine, and L-tyrosine to generate a sample comprising intermediate-1; treating the sample comprising intermediate-1 to partially depolymerize the protected copolymer and deprotect benzyl-protected L-glutamic acid, measuring the viscosity of the sample comprising intermediate-1 during the treatment, and ending the treatment when the viscosity of the sample correlates to generation of glatiramer acetate with a molecular mass of about 5000 Da-9000 Da, thereby generating a sample comprising intermediate-2; treating the sample comprising intermediate-2 to deprotect TFA-protected L-lysine, thereby generating intermediate-3; further processing the intermediate-3 to generate a sample glatiramer acetate; and purifying the glatiramer acetate to generate a composition comprising purified glatiramer acetate having a Mp of 5000-9000 Da.

In some embodiments, the methods include measuring the viscosity of the sample comprising intermediate-1 at least once during the treatment (e.g., depolymerization reaction), continuously during the treatment (e.g., depolymerization reaction), and/or intermittently during the treatment (e.g., depolymerization reaction), for example at one second intervals or intervals greater than one second. In some embodiments, methods include measuring the viscosity of the sample comprising intermediate-1 in at least one (e.g., 1, 2, 3, 4, 5, less than 10, less than 20, less than 50, less than 100, less than 500, or less than 1000) sample(s) obtained during the treatment. Samples can be obtained intermittently during the treatment (e.g., depolymerization reaction), for example at one second intervals or intervals greater than one second.

In some embodiments, an endpoint range of viscosity in the depolymerization reaction solution defines or signals when action should be taken during the depolymerization reaction. Suitable viscosity levels for use as an endpoint range include, for example, a viscosity level in the depolymerization reaction solution of about 77 cP-566 cP and/or a level or range of viscosity shown in Table 1 and/or FIG. 2.

Figure 2:
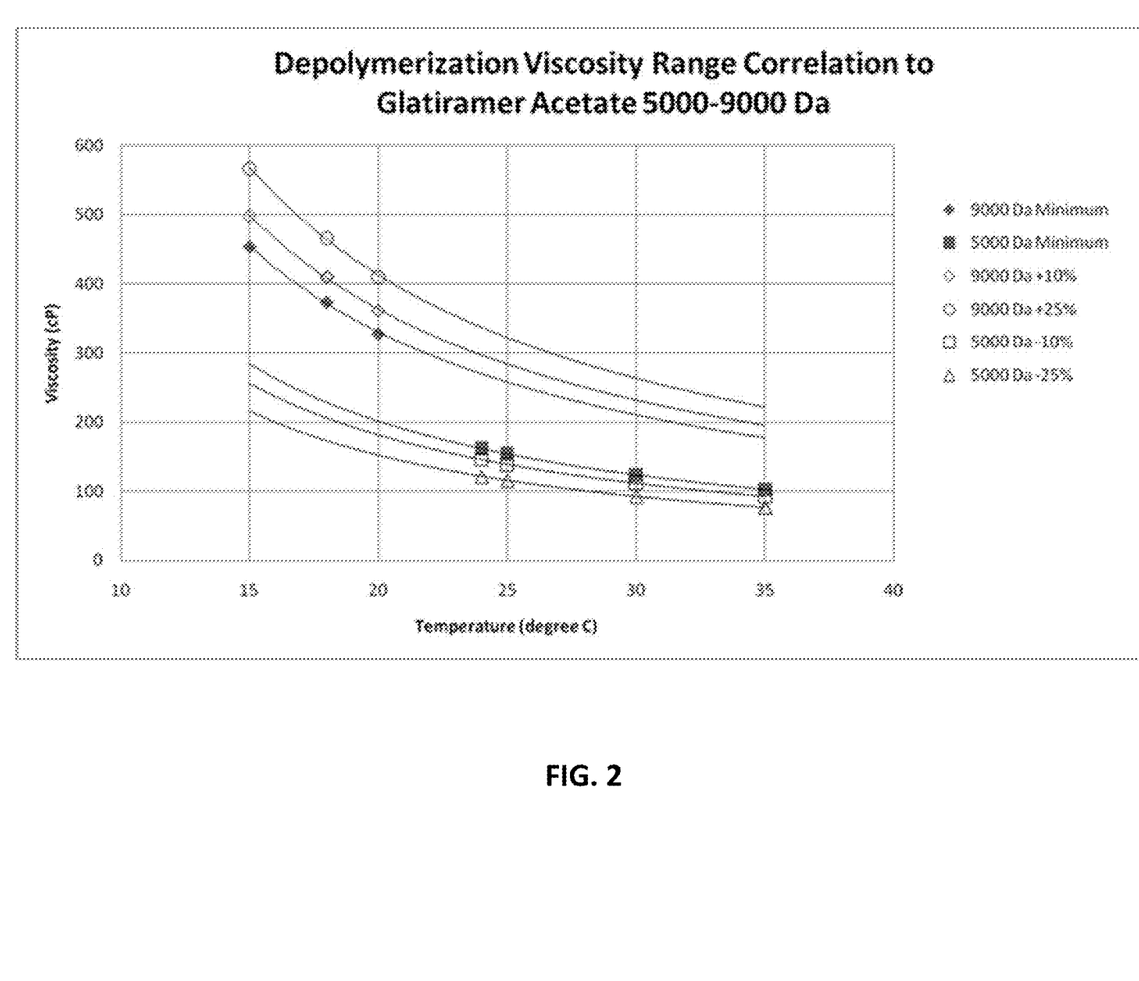
FIG. 2|Graphical representation of the depolymerization viscosity-temperature Correlation to glatiramer acetate with a molar mass of about 5000-9000 Da.

In some embodiments, action is taken during the depolymerization reaction when a level of viscosity is assessed in the depolymerization reaction solution that correlates to the production of glatiramer acetate with a peak average molecular mass of about 5000 Da-9000 Da, e.g., when the viscosity is at about 77 cP-566 cP and/or at a level or range of viscosity shown in Table 1 and/or FIG. 2.

In some embodiments, methods include conducting, performing, or carrying out the depolymerization reaction at a controlled temperature. Suitable temperatures can include, for example, about 15° C. to about 35° C., about 18° C. to about 35° C., about 18° C. to about 30° C., and/or about 18° C. to about 22° C., and/or a temperature shown in FIG. 2.

In some embodiments, a composition comprising purified glatiramer acetate is an active pharmaceutical ingredient or drug product. In some embodiments, treating the sample comprising intermediate-1 comprises using a solution comprising phenol and hydrogen bromide and acetic acid. In some embodiments, N-carboxy anhydrides of L-alanine, benzyl-protected L-glutamic acid, trifluoroacetic acid (TFA)-protected L-lysine, and L-tyrosine are polymerized in predetermined ratios to generate intermediate-1 using diethylamine as an initiator. In some embodiments, treating the sample comprising intermediate-2 to deprotect TFA-protected L-lysine comprises contacting the sample comprising intermediate-2 with aqueous piperidine.

Also described herein is a method for manufacturing glatiramer acetate drug substance having a Mp of 5000-9000 Da, the method comprising: (a) polymerizing N-carboxy anhydrides of L-alanine, benzyl-protected L-glutamic acid, trifluoroacetic acid protected L-lysine and L-tyrosine to generate a composition comprising intermediate-1; (b) treating the composition comprising intermediate-1 to partially depolymerize intermediate-1 and to deprotect benzyl-protected L-glutamic acid; (c) measuring the viscosity of the composition during step (b); (d) ending step (b) when the viscosity of the composition is at a predetermined level that informs that step (b) will yield intermediate-2 having a desired peak average molecular weight, thereby generating a composition comprising intermediate-2; (e) treating the composition comprising intermediate-2 to deprotect trifluoroacetic acid protected L-lysine, thereby generating a composition comprising intermediate-3; and (f) processing the composition comprising intermediate-3 to generate glatiramer acetate drug substance having a Mp of 5000-9000 Da.

In some instances, methods include comparing reaction solution viscosity to a reference standard of reaction solution viscosity to assess suitability for undergoing a next step in the reaction, e.g., as disclosed herein. In some instances, methods include recording reaction solution viscosity in a print or computer-readable medium, e.g., in a test report, Material Safety Data Sheet (MSDS) or Certificate of Testing or Certificate of Analysis (CofA).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

A process for the manufacture of glatiramer acetate generally includes the following:

Polymerization of N-carboxy anhydrides of L-alanine, benzyl-protected L-glutamic acid, trifluoroacetic acid (TFA) protected L-lysine and L-tyrosine (collectively referred to as NCAs) to result in a protected copolymer (Intermediate-1);

Depolymerization and benzyl deprotection of Intermediate-1, e.g., using hydrobromic acid in acetic acid (e.g., phenol treated 33% HBr/acetic acid) to generate Intermediate-2; and Deprotection of the TFA-protected lysines on Intermediate-2 (e.g., by treatment with piperdine) to create Intermediate-3, followed by processing to generate glatiramer acetate and further purification and drying of the isolated glatiramer acetate drug substance.

During polymerization, the NCAs are co-polymerized in a predetermined ratio using diethylamine as an initiator. Upon consumption of the NCA components, the reaction solution is quenched in water. The resulting protected polymer (Intermediate-1) is isolated and dried. During depolymerization and benzyl deprotection, Intermediate-1 is treated with phenol-treated 33% HBr in acetic acid (HBr/AcOH). This results in the cleavage of the benzyl protecting group on the glutamic acids as well as cleavage of peptide bonds throughout the polymer. After a period of time the reaction is quenched with water, and the product polymer is isolated by filtration and washed with water. The product polymer, Intermediate-2, has a reduced molecular weight relative to Intermediate-1. Intermediate-2 can be dried before proceeding to deprotection of TFA-protected lysine. During deprotection TFA-protected lysines, Intermediate-2 is treated with aqueous piperidine to remove the trifluoroacetyl group on the lysine. The resulting copolymer, Intermediate-3, is subsequently purified using diafiltration/ultrafiltration and the resulting acetate salt is dried to produce glatiramer acetate drug substance. Exemplary methods for the manufacture of glatiramer acetate are known in the art (see, for example, U.S. Pat. No. 3,849,550; WO 95/031990, US 2006/0154862, US 2007/0021324, US 2010/0256039, US 2007/0021324, US 2009/0263347, and US 2010/0256039, WO 2010/115175, and WO 2010/017292 which are hereby incorporated by reference in their entirety).

The present disclosure is based, at least in part, on the discovery of a correlation between reaction solution viscosity in the depolymerization reaction described above and molecular mass of glatiramer acetate, e.g., resulting from the process. Use of this correlation in the manufacture or production of glatiramer acetate, via in-process or real-time assessment of reaction solution viscosity, allows for in-process or real-time tracking of the progress and/or level of completion of the depolymerization reaction and/or provides accurate and reproducible information regarding the molecular weight of glatiramer acetate resulting from the process. Use of the correlation also allows for action to be taken with respect to the depolymerization reaction, e.g., based on the progress or level of completion of the depolymerization reaction and/or the correlation between viscosity and the molecular mass of glatiramer acetate. For example, the depolymerization reaction can be terminated (e.g. automatically or manually) upon detection of a defined level of completion and/or upon detection of a level or range of viscosity that correlates to a molecular mass of glatiramer acetate that will result from the process.

Accordingly, the present disclosure allows improved monitoring of the manufacture or production of glatiramer acetate and thus can be used to maintain consistency of the manufacture or production of glatiramer acetate, e.g., within batches and/or between different batches.

Viscosity is a measure of the resistance of a fluid which is being deformed by either shear stress or tensile stress. Viscosity is a measure of fluid friction. The present disclosure provides methods for in-process or real-time assessment (e.g., monitoring, measurement, analysis, detection, determination, evaluation, and/or estimation) of the viscosity of the reaction solution during the depolymerization reaction used in the manufacture or production of glatiramer acetate. Using the correlation disclosed herein, data obtained from this in-process or real-time assessment is used to determine, in real-time, the progress or level of completion of the depolymerization reactions and/or the molecular mass of glatiramer acetate that will result from the process. For example, action can be taken upon detection of a defined level of completion and/or upon detection of a level of viscosity that correlates to the production of glatiramer acetate with defined molecular mass.

In some instances, action can be taken when in-process or real-time assessment of the viscosity of the reaction solution during the depolymerization reaction detects or signals a level of viscosity of the reaction solution of about 77 centipoise (cP)-566 cP (e.g., a level of viscosity that correlates to the production of glatiramer acetate with a molecular mass of about 5000 Da-9000 Da).

In some instances, action can be taken when in-process or real-time assessment of the viscosity of the reaction solution during the depolymerization reaction detects or signals a level of viscosity of the reaction solution (e.g., a level of viscosity that correlates to the production of glatiramer acetate with a molecular mass of about 5000 Da-9000 Da) shown in Table 1 and/or FIG. 2 at a reaction solution temperature shown in Table 1 and/or FIG. 2.

TABLE 1

Reaction Solution Viscosity

| Reaction Solution Temperature (° C.) | Viscosity (cP) |
|---|---|
| 15-35 | 103-453[a] |
|  | 77-566[b] |
|  | 93-498[c] |
| 18-35 | 103-373[a] |
|  | 77-466[b] |
|  | 93-410[c] |
| 18-30 | 124-373[a] |
|  | 93-466[b] |
|  | 112-410[c] |
| 18-25 | 154-373[a] |
|  | 116-466[b] |
|  | 139-410[c] |
| 20-24 | 162-328[a] |
|  | 122-410[b] |
|  | 146-361[c] |

[a]refer to minimum and maximum values
[b]shows minimum value[a] × 0.75 and maximum value[a] × 1.25
[c]shows minimum value[a] × 0.9 and maximum value[a] × 1.1

Figure 1:
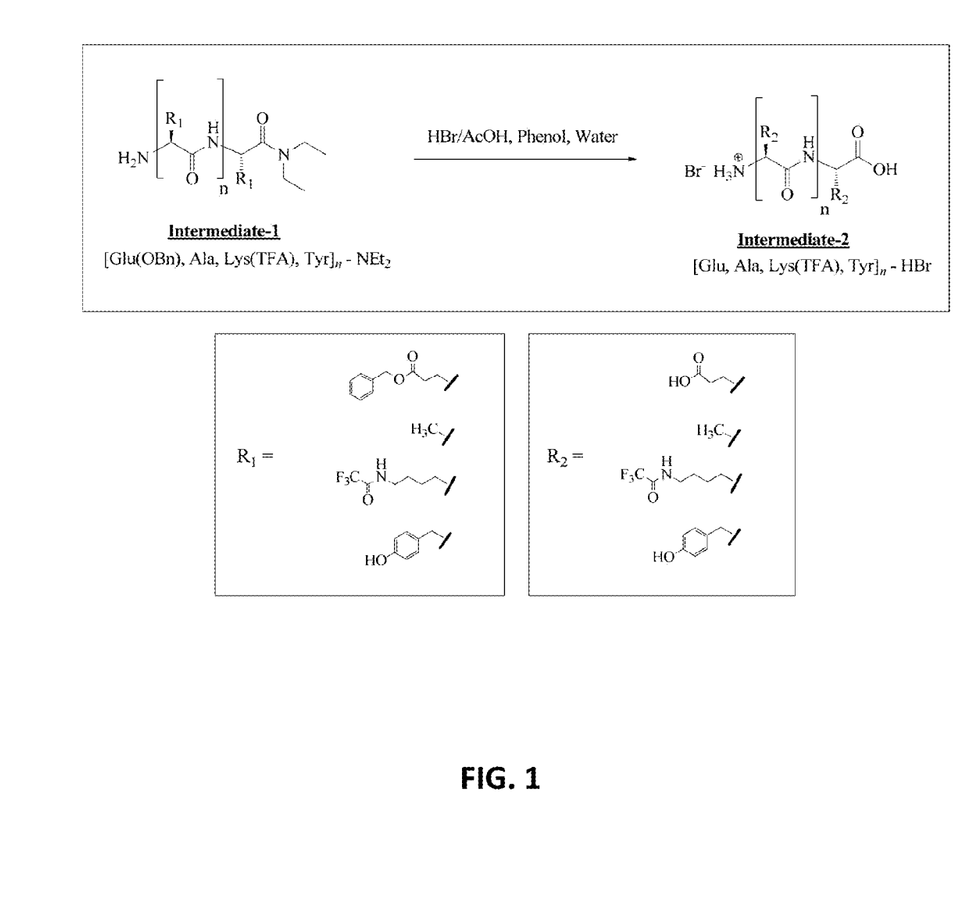
FIG. 1|Reaction scheme of glatiramer acetate Intermediate-2.

In some instances, a level of viscosity of the reaction solution of 77 cP-566 cP or a level of viscosity shown in Table 1 and/or FIG. 1 signals a level of completion of the depolymerization reaction suitable for advancement of the process to the deprotection of the TFA-protected lysines on Intermediate-2 reaction, e.g., such that the process will yield glatiramer acetate with a molecular weight (e.g., peak average molecular weight) of about 5000-9000 Da, e.g. about 5000 Da, 6000 Da, 7000 Da, 7300 Da, 8000 Da, or 9000 Da.

In some instances, a level of viscosity of the reaction solution of 77 cP-566 cP or a level of viscosity shown in Table 1 and/or FIG. 2 that signals a level of completion of the depolymerization reaction suitable for advancement of the process to the deprotection of the TFA-protected lysines on Intermediate-2 reaction, e.g., such that the process will yield glatiramer acetate with a molecular weight (e.g., mean molecular weight) of about 5000-9000 Da is referred to herein as an 'endpoint range.'

Viscosity can be expressed in any suitable units. For example, viscosity can be expressed in terms of kinematic viscosity, dynamic viscosity, absolute viscosity, apparent viscosity, intrinsic viscosity, relative viscosity, or specific viscosity. In addition, units can be converted to facilitate comparison with viscosity units provided herein, e.g., in Table 1 and/or FIG. 2, using reasonable skill. Unless otherwise specified, the viscosity values noted herein are dynamic viscosity values.

In some instances, action can be taken if a level of viscosity of a reaction solution falls within, correlates with, is equal (e.g., about equal) to, and/or is equivalent (e.g., about equivalent) to, a viscosity unit or range shown in Table 1 and/or FIG. 2.

Action can include, but is not limited to, for example, termination of the depolymerization reaction and either advancement to the next step in the process or abandonment of the process (e.g., a preparation of equipment for a new cycle), sample removal, and/or alteration of reaction conditions. Termination of the depolymerization reaction can include quenching the reaction solution in water. Action can be automated or manual. The methods described herein can also include selecting to discard, withhold, reprocess through a previous manufacturing step, or discontinue use of a polymeric precursor of glatiramer acetate, for example, if the viscosity of the reaction solution does not meet a preselected relationship, are not equal to, are not equivalent with, and/or are not consistent with the levels shown in Table 1 and/or FIG. 2.

In some instances, methods can include controlling (e.g., compensating for, reference to, control of, and/or normalization towards) process parameters or variables that can impact the in-process assessment of viscosity. For example, methods can include compensating for process parameters or variables that would otherwise lead to inconsistent viscosity values. Process parameters or variables that can controlled include, for example, the molecular weight of the polymeric precursors of glatiramer acetate in the test reaction solution, the temperature of the reaction solution, the concentration of polymeric precursors of glatiramer acetate in the reaction solution, and/or the density of the reaction solution (the density of a fluid can be obtained, for example, by dividing the mass of the fluid by the volume of the fluid. Density is normally expressed as kg per cubic meter). Control of such parameters can include for example, conversion of assessed viscosity levels (e.g. post assessment) to provide comparable levels, and/or selection and/or use of comparable process parameters or variables in the production and/or manufacture of glatiramer acetate (e.g., in the depolymerization reaction). Conversion of assessed viscosity levels can be performed using methods and calculations known in the art. Use of comparable process parameters or variables can include selection of one or more of conditions for reaction solution temperature range, reaction solution concentration range, reaction solution density range, and/or raw material quality. Such selections can be made prior to or contemporaneously with the depolymerization and benzyl deprotection of Intermediate-1. Suitable reaction solution temperature ranges for use in the manufacture or production of glatiramer acetate can include, for example, a reaction solution temperature range sufficient to generate glatiramer acetate with a molecular weight (e.g., peak average molecular weight) of about 5000-9000 Da and a level of viscosity of the depolymerization reaction solution of about 77 cP-566 cP or at a level of viscosity shown in Table 1 and/or FIG. 2, a temperature range of about 15° C.-35° C., a temperature range shown in Table 1, and/or temperatures of, for example, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50° C., or more than 50° C. Suitable reaction solution concentration ranges include, for example, concentration ranges sufficient to generate glatiramer acetate with a molecular weight (e.g., peak average molecular weight) of about 5000-9000 Da and a level of viscosity of the depolymerization reaction solution of about 77 cP-566 cP or at a level of viscosity shown in Table 1 and/or FIG. 2, concentration ranges of about, for example, 1-20, 1-15, 5-15, 5-10, 7.5-10, 9-10, 9.0-9.5%, and/or concentrations of, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 wt./wt., relative to the Intermediate-1 starting material. Suitable reaction solution density ranges include, for example, density ranges sufficient to generate glatiramer acetate with a molecular weight (e.g., peak average molecular weight) of about 5000-9000 Da and a level of viscosity of the depolymerization reaction solution of about 77 cP-566 cP or at a level of viscosity shown in Table 1 and/or FIG. 2, density ranges of about for example, 0.1-10 g/mL, 0.5-10 g/mL, 1.0-10 g/mL, 1.0-5.0 g/mL, 1.0-4.0 g/mL, 1.0-3.0 g/mL, and 1.0-2.0 g/mL. Other process parameters or variables may also be varied or controlled to produce comparable viscosity levels using techniques known in the art.

In general, the term 'about' can include variation from a stated value of +/−0.01, 0.1, 0.5, 1, 2, 3, 4, 5, 6, 7, 8, 9, 10, and or +/−1%, 10%, 50%, 100% of the stated value. As used herein and with respect to molecular weight, the term 'about' can include +/−1, 10, 50, 100, 250, 500, and 750 Da. As used herein and with respect to units of viscosity, the term 'about' can include, for example, plus or minus 0.01, 0.1 0.5, 1, 2, 3, 4, 5, 6 7, 8, 9, 10, 11, 12, 13, 14, 15, 16, 17, 18, 19, 20, 25, 30, 35, 40, 45, 50, 55, 60, 65, 70, 75, 80, 85, 90, 95 100, 150, 200, 250, 500 or 1000 cP, or equivalents thereof. As used herein and with respect to units of temperature, the term 'about' can include, for example, plus or minus 0.01, 0.1 0.5, 1, 2, 3, 4, 5, 6 7, 8, 9, and 10° C., or more than 10° C.

Polymeric precursors of glatiramer acetate can include but are not limited to, e.g., Intermediate-1, Intermediate-2, and/or Intermediate-3, described in the manufacturing process above. For example, polymeric precursors of glatiramer acetate can include peptides generated during the production of glatiramer acetate, e.g., following the initiation step and up to the lysine deprotection step.

A composition containing glatiramer acetate and/or glatiramer acetate, as used herein, can be a drug substance (DS) (also known as an active pharmaceutical ingredient (API), a drug product (DP), or a process intermediate. Glatiramer acetate can also include glatiramer acetate before or after formulation as a drug product.

The term "amino acid" is not limited to naturally occurring amino acids, but can include amino acid derivatives and/or amino acid analogs. For example, in an amino acid copolymer comprising tyrosine amino acids, one or more of the amino acids can be a homotyrosine. Further, a peptide having one or more non-peptide or peptidomimetic bonds between two adjacent residues is included within the scope of this disclosure.

Molar mass is defined as Mp, which is the average molar mass at the peak of the SEC-MALS analysis distribution. While the disclosure refers to peak average molar mass and/or Mp, a person of skill in the art will appreciate that other units of mass are encompassed and can be determined from the values provided herein using routine skill.

Methods for In-Process Assessment of Viscosity

Viscosity can be assessed using any method known in the art that permits in-process and/or real-time assessment of viscosity.

Viscometry can be used as an in-process method, during the manufacture or production of glatiramer acetate, for assessing reaction solution viscosity during the depolymerization reaction of a glatiramer acetate manufacture or production process. For example, viscometry can be used to assess depolymerization reaction progress from Intermediate-1 to Intermediate-2 during the depolymerization and benzyl deprotection of Intermediate-1.

Viscometers suitable or adaptable for the methods described herein are known in the art and include, but are not limited to, for example, glass capillary kinematic viscometers, spindle-type viscometers, and resonant or vibrational viscometers.

In-process use of viscometers requires submersion of the viscometer in the reaction solution during the manufacture or production of glatiramer acetate, e.g., at least during the depolymerization reaction of a glatiramer acetate manufacture or production process. In some instances, suitable viscometers include a temperature sensor that can operate with (e.g., simultaneously with) the viscometer. Use of such viscometers can allow simultaneous assessment of viscosity and temperature.

In-process acquired viscosity units can alter (e.g., decrease) over time (e.g., as the depolymerization reaction progresses). In-process acquired viscosity units can also fluctuate, for example, upon variations in temperature.

In some instances, methods can include assessment of viscosity alone or in combination with temperature. In some instances, viscosity and temperature are assessed simultaneously in-process. In some instances a sample may be removed from the reaction vessel and analyzed for viscosity and temperature with or without further sample processing outside of the production process (e.g. off-line testing).

In some instances, viscometry of a depolymerization reaction solution can include obtaining one or more measurements (e.g. 1, 2, 3, 4, 5, 6, 7, 8, 9, 10, 11, 12, 13, 14, 15, 16, 17, 18, 19, 20 or more measurements, including 1, 2, 3, 4, 5, 6, 7, 8, 9, 10, 11, 12, 13, 14, 15, 16, 17, 18, 19, 20 measurements per hour bi-hourly, or at other scheduled intervals) taken at one or more intervals during the manufacture or production of glatiramer acetate, e.g., during the depolymerization reaction. Where more than one measurement is made, average values or mean values can be calculated to determine viscosity of the reaction solution. Such values can be compared, for example, to the values shown in Table 1. In some instances, viscometry can include real-time monitoring of viscosity and action can be taken when viscosity of the reaction sample is equivalent to a value or range shown in Table 1. Alternatively or in addition, viscometry of a reaction solution can include a mean value of a number of readings, for example, a number of readings assessed over a defined period of time. Suitable periods of time can include, for example, 1 second, 5 seconds, 10 seconds, 30 seconds, 1 minute, 2 minutes, 5 minutes, 10 minutes, 30 minutes, 45 minutes, 1 hour, 6 hours, 12 hours, 24 hours, 48 hours, or more than 48 hours and ranges between any two of these time points. Raw data, e.g., assessed viscometry units can be analyzed using techniques known in the art, including, for example, statistical analysis. Molar mass can be determined using methods known in the art, for example, SEC-MALS analysis, and/or the molecular weight markers and/or methods disclosed in U.S. Pat. No. 6,800,287, which is hereby incorporated by reference in its entirety.

Other methods not explicitly disclosed herein may also be used so long as they allow at least detection (e.g., specific detection) of reaction solution viscometry.

Steps recited herein do not indicate or imply order. Accordingly, the steps can be performed in any order that allows a result to be obtained.

EXAMPLES

The invention is further described in the following examples, which do not limit the scope of the invention described in the claims.

FIG. 1 illustrates the depolymerization and deprotection of Intermediate-1 to generate Intermediate-2.

A number of glatiramer acetate production processes were run at various temperatures to generate glatiramer acetate with an Mp of 5000 Da-9000 Da at about 15° C.-35° C. Viscosity and temperature were simultaneously assessed in-process during the depolymerization and deprotection of Intermediate-1. Results are shown in FIG. 2.

What is claimed is:

1. A method for manufacturing glatiramer acetate drug substance having a Mp of 5000-9000 Da, the method comprising:
   (a) polymerizing N-carboxy anhydrides of L-alanine, benzyl-protected L-glutamic acid, trifluoroacetic acid protected L-lysine and L-tyrosine to generate a composition comprising intermediate-1;
   (b) treating the composition comprising intermediate-1 to partially depolymerize intermediate-1 and to deprotect benzyl-protected L-glutamic acid;
   (c) intermittently or continuously measuring the viscosity of the composition during step (b);
   (d) ending step (b) when the viscosity of the composition measured during step (b) is at a predetermined level that informs that step (f) will yield glatiramer acetate with a Mp of 5000-9000 Da, thereby generating a composition comprising intermediate-2;
   (e) treating the composition comprising intermediate-2 to deprotect trifluoroacetic acid protected L-lysine, thereby generating a composition comprising intermediate-3; and
   (f) processing the composition comprising intermediate-3 to generate glatiramer acetate drug substance having a Mp of 5000-9000 Da.

2. The method of claim 1 wherein viscosity is measured in-process during step (b).

3. The method of claim 1 wherein the viscosity is measured intermittently during step (b).

4. The method of claim 1 wherein the viscosity is measured continuously during at least a portion of step (b).

5. The method of claim 1 wherein the viscosity is measured continuously during a substantial portion of step (b).

6. The method of claim 1 wherein the viscosity is measured continuously during step (b).

7. The method of claim 1 wherein the predetermined level of viscosity is 77 cP to about 566 cP when viscosity is measured at 15° C. to 35° C.

8. The method of claim 1, wherein the predetermined level of viscosity is 93 cP to about 498 cP at 15° C. to 35° C.

9. The method of claim 1, wherein the predetermined level of viscosity is 103 cP to about 453 cP at 15° C. to 35° C.

10. The method of claim 7, wherein the predetermined level of viscosity is 77 cP to about 566 cP when viscosity is measured at 15° C. to 35° C. and the density of the composition is 0.8-1.6 gm/ml.

11. The method of claim 7, wherein the predetermined level of viscosity is 77 cP to about 566 cP when viscosity is measured at 15° C. to 35° C. and the density of the composition is 1.0-1.4 gm/ml.

12. The method of claim 1 wherein the temperate of the composition during step (b) is 15° C.-35° C.

13. The method of claim 1 where in the temperature of the composition during step (b) is 19° C.-25° C.

14. The method of claim 1 wherein the concentration of Intermediate-1 at the start of step (b) is 7-11% on a weight/weight basis.

15. The method of claim 1 wherein the density of the composition during step (b) is 0.8-1.6 gm/ml.

16. The method of claim 1, further comprising measuring the temperature of the composition during step (b).

17. The method of claim 16, wherein both viscosity and temperature are measured continuously during step (b).

18. The method of claim 1 wherein step (b) is ended when the viscosity of the composition is at a predetermined level that informs that step (f) will yield glatiramer acetate with a Mp of 7000-8000 Da.

19. The method of claim 1, wherein step (b) is ended when the viscosity of the composition is at a predetermined level that informs that step (f) will yield glatiramer acetate with a Mp of 7200-7400 Da.

20. The method of claim 1 wherein step (b) comprises treating the composition comprising Intermediate-1 with phenol, HBr and acetic acid.

21. The method claim 1 wherein step (d) comprises quenching the reaction with water.

22. The method of claim 1 wherein Intermediate-1 is present at 7-11% on a weight/weight basis at the start of step (b).

23. The method of claim 1 wherein water is present in the composition during step (b).

24. The method of claim 23 wherein water is present at 0.1-10% on a weight/weight basis relative to the entire reaction.

25. The method of claim 24 wherein step (b) is carried out at 19° C.-25° C., water is present at 0.1%-10% on a weight/weight basis relative to the entire reaction and Intermediate-1 is present at 7%-11% on a weight/weight basis at the start of step (b).

26. The method of claim 1, wherein step (f) comprises filtering the composition comprising intermediate-3.

27. A method for preparing glatiramer acetate drug product, the method comprising combining the glatiramer acetate drug substance prepared by the method of claim 1 with mannitol.

28. The method of claim 27, further comprising packaging the glatiramer acetate drug product.

29. The method of claim 1 comprising ending step (b) when the viscosity of the sample is within a range shown in Table 1 when measured within a corresponding temperate range shown in Table 1.

30. The method of claim 1 wherein water is present in the composition during step (b) in a range selected from the group consisting of 5-25%, 13-19%, and 14-18% w/w against Intermediate-1 present at the start of step (b).

* * * * *